United States Patent
Rosen

(10) Patent No.: US 7,238,680 B2
(45) Date of Patent: Jul. 3, 2007

(54) TOPICAL COMPOSITIONS FOR VETERINARY USES

(76) Inventor: Steven E. Rosen, 2150 SW. 90th Ave., Unit A, Ft. Lauderdale, FL (US) 33324

( * ) Notice: Subject to any disclaimer, the term of this patent is extended or adjusted under 35 U.S.C. 154(b) by 179 days.

(21) Appl. No.: 10/161,552

(22) Filed: Jun. 3, 2002

(65) Prior Publication Data

US 2003/0077308 A1    Apr. 24, 2003

Related U.S. Application Data

(60) Provisional application No. 60/298,128, filed on Jun. 13, 2001, provisional application No. 60/295,093, filed on Jun. 1, 2001.

(51) Int. Cl.
*A61K 31/60*    (2006.01)
(52) U.S. Cl. .................. 514/165; 119/601; 424/60; 424/73; 424/78.05; 424/78.06; 424/78.07; 424/401; 514/532; 514/533; 514/534; 514/887; 514/937
(58) Field of Classification Search ................ 424/400, 424/401, 405, 484, 43, 45, 59, 60–64, 73, 424/78.05, 78.06, 78.07; 514/165, 817, 818, 514/829, 830, 856–865, 887, 937
See application file for complete search history.

(56) References Cited

U.S. PATENT DOCUMENTS

| | | | |
|---|---|---|---|
| 3,136,696 A | 6/1964 | Harrison et al. | |
| 3,530,217 A | 9/1970 | White et al. | |
| 3,928,561 A | 12/1975 | Baldwin | |
| 3,981,681 A | 9/1976 | de la Guardia | |
| 4,126,681 A | 11/1978 | Reller | |
| 4,185,100 A | 1/1980 | Rovee et al. | |
| 4,199,576 A | 4/1980 | Reller et al. | |
| 4,219,548 A | 8/1980 | Reller | |
| 4,228,163 A | 10/1980 | Bliss | |
| 4,244,948 A * | 1/1981 | Boghosian et al. | 424/230 |
| 4,363,796 A | 12/1982 | Bouillon et al. | |
| 4,364,940 A | 12/1982 | Neiss et al. | |
| 4,369,180 A | 1/1983 | Mihalovits | |
| 4,505,935 A | 3/1985 | Larsson | |
| 4,525,344 A | 6/1985 | Tutsky | |
| 4,665,063 A | 5/1987 | Bar-Shalom | |
| 4,692,552 A | 9/1987 | Mueller et al. | |
| 4,708,866 A | 11/1987 | Turco et al. | |
| 4,775,530 A | 10/1988 | Perricone | |
| 4,908,355 A | 3/1990 | Gettings et al. | |
| 4,919,920 A | 4/1990 | Devos | |
| 4,937,370 A | 6/1990 | Sabatelli | |
| 4,946,870 A | 8/1990 | Partain, III et al. | |
| 4,999,186 A | 3/1991 | Sabatelli et al. | |
| 5,034,221 A | 7/1991 | Rosen et al. | |
| 5,041,282 A | 8/1991 | Sabatelli et al. | |
| 5,073,371 A | 12/1991 | Turner et al. | |
| 5,073,372 A | 12/1991 | Turner et al. | |
| 5,087,445 A | 2/1992 | Haffey et al. | |
| 5,138,089 A | 8/1992 | Sabatelli | |
| 5,204,093 A | 4/1993 | Victor | |
| 5,223,267 A | 6/1993 | Nichols | |
| 5,243,076 A | 9/1993 | Skidmore et al. | |
| 5,262,407 A | 11/1993 | Leveque et al. | |
| 5,326,566 A * | 7/1994 | Parab | 424/401 |
| 5,387,412 A | 2/1995 | Moore | |
| 5,585,109 A | 12/1996 | Hayward et al. | |
| 5,626,856 A | 5/1997 | Berndt | |
| 5,672,340 A | 9/1997 | Sun et al. | |
| 5,674,912 A | 10/1997 | Martin | |
| 5,688,495 A | 11/1997 | Rosen et al. | |
| 5,736,126 A | 4/1998 | Van Engelen et al. | |
| 5,747,021 A | 5/1998 | McKenzie et al. | |
| 5,750,093 A | 5/1998 | Menon et al. | |
| 5,788,956 A | 8/1998 | De Lacharriere et al. | |
| 5,824,666 A | 10/1998 | Deckner et al. | |
| 5,916,918 A * | 6/1999 | Konishi et al. | 514/546 |
| 5,917,088 A | 6/1999 | Philippe et al. | |
| 5,948,416 A | 9/1999 | Wagner et al. | |
| 6,001,340 A | 12/1999 | Rosen et al. | |
| 6,010,716 A | 1/2000 | Saunal et al. | |
| 6,156,299 A | 12/2000 | Rosen et al. | |
| 2003/0049212 A1* | 3/2003 | Robinson et al. | 424/59 |

FOREIGN PATENT DOCUMENTS

WO    WO 00/28958    5/2000

* cited by examiner

Primary Examiner—Neil S. Levy
(74) Attorney, Agent, or Firm—William R. Johnson

(57) ABSTRACT

A method of treating a non-human dermatological disorder, wherein the method comprises topically administering to a non-human dermatological disorder a therapeutically effective amount of a topical composition containing: (1) an active component comprising at least one salicylate derivative; and (2) at least one pharmaceutically acceptable solubilizer.

12 Claims, No Drawings

TOPICAL COMPOSITIONS FOR VETERINARY USES

CROSS REFERENCE TO RELATED APPLICATIONS

This application is related to and claims the benefit of U.S. Provisional Application Ser. No. 60/295,093, filed Jun. 1, 2001; and U.S. Provisional Application Ser. No. 60/298,128, filed Jun. 13, 2001. The entire disclosures of which are hereby incorporated by reference in there entirety for all purposes.

FIELD OF THE INVENTION

The present invention relates to topical compositions suitable for use in veterinary applications as well as methods for treating a variety of conditions employing such topical compositions.

BACKGROUND OF THE INVENTION

It is widely known that animals experience several dermatological ailments and disorders requiring veterinary assistance in order to promote healing and/or aid in the prevention thereof.

For example, animals who are shaved prior to an in-office surgery frequently develop ingrown hair and related skin irritations. If left alone, these areas can become what are commonly know as "hot spots." That is to say that the animal will likely start to pick at the affected area to the point of self-mutilation. Current treatment for this condition includes the use of steroid medications to quell the irritation. Since long-term use of these drugs is often needed to treat these conditions, the animal can develop secondary adrenal gland suppression, which in turn can lead to symptoms further related to the adrenal suppression.

Additionally, horses, cows and other animals are frequently prone to develop a sore that starts with a minor tear in the skin, such as from an abrasion. This opening in the skin can serve as in incubator for several species of flies and other insects that enter the wound and begin to lay eggs. This inhabitation by flies and other insects creates an enlarging ulceration in the skin that is characterized by a white chalky appearance. Commonly know as a "Florida sore," there currently is no known effective treatment for this disorder and it has further proven to be unresponsive to traditional antibiotic treatment.

Still another common ailment frequently encountered by the ungulates, or hoofed animals, such as horses, cows and the like, is the softening of the hoof. Specifically, animals with hooves often suffer from a softening of the base of the hoof, commonly referred to as the "frog," when subjected to constant moisture. The soreness associated with this problem can lead to limping and therefore, in severe instances, to subsequent musculoskeletal injuries.

In addition to the disorders previously described, there are several other dermatological disorders frequently experienced by animals, including such conditions as fungal infections, parasitic and bacterial infections, sunburn, warts and the like. To this end, there is a need in the art of veterinary medicine for a more effective methods of treating these and other common dermatological disorders encounters by animals.

SUMMARY OF THE INVENTION

Among other aspects, the present invention is based upon the surprising discovery that topical compositions comprising at least one salicylate derivative according to the invention are capable of being effectively used as topical formulations for a wide variety of veterinary purposes.

To that end, in one embodiment, the present invention relates to a method of treating a non-human dermatological disorder, wherein the method comprises topically administering to a non-human dermatological disorder a therapeutically effective amount of a topical composition containing: (1) an active component comprising at least one salicylate derivative; and (2) at least one pharmaceutically acceptable solubilizer. The active component(s) are preferably present in a therapeutically effective amount to prevent, treat or aid in the healing of a non-human dermatological disorder.

In another embodiment, the present invention relates to a method of preventing insects from inhabiting a non-human wound, the method comprising topically administering to a non-human wound a therapeutically effective amount of a topical composition containing: (1) an active component comprising at least one salicylate derivative; and (2) and at least one pharmaceutically acceptable solubilizer.

In still another embodiment, the present invention further provides a method of preventing insect bites, the method comprising topically administering to a non-human animal an effective amount of a topical composition containing: (1) an active component comprising at least one salicylate derivative; and (2) at least one pharmaceutically acceptable solubilizer.

In another embodiment, the present invention also provides a method of treating a softened ungulate hoof, the method comprising topically administering to a softened hoof a therapeutically effective amount of a topical composition containing: (1) an active component comprising at least one salicylate derivative; and (2) at least one pharmaceutically acceptable solubilizer.

In still another embodiment, the present invention provides a method of reducing the flow of blood from a bleeding, non-human animal wound, the method comprising topically administering to a non-human wound a therapeutically effective amount of a topical composition containing: (1) an active component comprising at least one salicylate derivative; and (2) at least one pharmaceutically acceptable solubilizer.

Additional advantages of the invention will be obvious from the description, or may be learned by practice of the invention. Additional advantages of the invention will also be realized and attained by means of the elements and combinations particularly pointed out in the appended claims. Therefore, it is to be understood that both the foregoing general description and the following detailed description are exemplary and explanatory of certain embodiments of the invention, and are not restrictive of the invention as claimed.

DETAILED DESCRIPTION OF THE INVENTION

The present invention may be understood more readily by reference to the following detailed description and any examples provided herein. It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular forms "a," "an," and "the" comprise plural referents unless the context clearly dictates otherwise. For example, reference to a component in the singular is intended to comprise a plurality of components.

Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about," it will be understood that the particular value forms another embodiment.

As used herein, the term "dermatological" is intended to refer to any aspect of the physiology and pathology of non-human animal skin; including several skin components as the dermis and epidermis.

As used herein, the term "dermis" is intended to refer to the sensitive connective tissue layer of skin located below the epidermis. The dermis often contains nerve endings, sweat and sebaceous glands, and blood and lymph vessels.

As used herein, the term "epidermis" refers to an outer, protective nonvascular layer of skin covering the dermis.

As used herein, the term "non-human animal" is intended to refer to any known animal commonly treated by veterinary medicine. In one aspect, the non-human animal is any one or more of the known livestock animals, including such animals as cattle, bison, pigs, and fowl. In an alternative aspect, a non-human animal includes any one or more of the known zoo animals, including without limitation, animals such as primates; ungulates; reptiles; marsupials; giraffes; tigers; lions; and the like. In still another aspect, the non-human animal includes any one or more of the commonly known house and/or farm pets; including animals such as dogs, cats, horses, ferrets and the like.

As used herein, the term "alkyl" refers to a paraffinic hydrocarbon group which may be derived from an alkane by dropping one hydrogen from the formula. Non-limiting examples include methyl, ethyl, propyl, isopropyl, butyl, t-butyl, and isobutyl. To this end, it should be understood that an alkyl substituent suitable for use in the present invention can be a branched or straight chain alkyl substituent.

As used herein, the term "alkenyl" is intended to refer to a substituent derived from the class of unsaturated hydrocarbons having one or more double bonds. Those containing only one double bond are referred to as alkenes or alkenyl substituents. Those with two or more double bonds are called alkadienes (alkadienyl), alkatrienes (alkatrienyl) and so on. Non-limiting examples include ethylene, propylene, butylene and the like. To this end, it should be understood that an alkenyl substituent suitable for use in the present invention can be substituted or unsubstituted.

As used herein, the term "alkynyl" is intended to refer a substituent derived from the class of unsaturated hydrocarbons having one or more triple bonds.

As used herein, the term "salicylate derivative" is intended to refer to salicylate derivative of the generic formula:

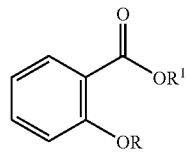

wherein R and R$^1$ are independently selected from the group comprising an electron; hydrogen; branched or straight chain $C_1$-$C_{12}$ alkyl; branched or straight chain $C_2$-$C_{12}$ alkenyl; branched or straight chain $C_2$-$C_{12}$ alkynyl; substituted or unsubstituted $C_3$-$C_7$ cycloalkyl; substituted or unsubstituted aryl; substituted or unsubstituted arylalkyl; the group I metals; the group II metals; choline; triethanolamine; and a carbonyl moiety having the general formula —(CO)—R$^2$, wherein R$^2$ is selected from hydrogen; branched or straight chain $C_1$-$C_{12}$ alkyl; branched or straight chain $C_2$-$C_{12}$ alkenyl; branched or straight chain $C_2$-$C_{12}$ alkynyl; substituted or unsubstituted $C_3$-$C_7$ cycloalkyl; substituted or unsubstituted aryl; and substituted or unsubstituted arylalkyl.

As used herein, the term "aryl" refers to a compound or substituent whose molecules have the ring structure characteristic of benzene, naphthalene, phenanthrene, anthracene, and the like. That is to say, an aryl group typically contains either the 6-carbon ring of benzene or the condensed 6 carbon rings of other aromatic derivatives. For example, an aryl group can be a phenyl or naphthyl group. To this end, it should be understood that aryl substituents suitable for use with the present invention can be substituted or unsubstituted.

As used herein, the term "arylalkyl" refers to a compound or substituent containing both aliphatic and aromatic structures.

As used herein, the term "pharmaceutically acceptable" refers to any one or more component that has been deemed suitable for use in one or more types of drugs, medicinal and curative products, also including components deemed suitable for use in ancillary products such as tonics, shampoos, conditioners, repellents, dietary supplements, vitamins, deodorants, and the like.

As used herein, the phrase "group I metals" refers to the class of metals including lithium, sodium, potassium, rubidium, cesium and francium.

As used herein, the phrase "group II metals" refers to the class of metals including beryllium, magnesium, calcium, strontium, barium, and radium.

As discussed above, the methods according to the present invention involve the use of a topical composition comprising an active component in a pharmaceutically acceptable solubilizer. To that end, the active component comprises at least one salicylate derivative of the generic formula:

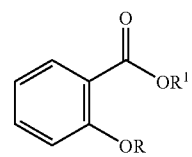

wherein R and R$^1$ are independently selected from the group comprising an electron; hydrogen; branched or straight chain $C_1$-$C_{12}$ alkyl; branched or straight chain $C_2$-$C_{12}$ alkenyl; branched or straight chain $C_2$-$C_{12}$ alkynyl; substituted or unsubstituted $C_3$-$C_7$ cycloalkyl; substituted or unsubstituted arylalkyl; substituted or unsubstituted aryl; the group I metals; the group II metals; choline; triethanolamine; and a carbonyl moiety having the general formula —(CO)—R$^2$, wherein R$^2$ is selected from hydrogen; branched or straight chain $C_1$-$C_{12}$ alkyl; branched or straight chain $C_2$-$C_{12}$ alkenyl; branched or straight chain $C_2$-$C_{12}$ alkynyl; substituted or unsubstituted $C_3$-$C_7$ cycloalkyl; substituted or unsubstituted arylalkyl; and substituted or unsubstituted aryl.

Specific examples of suitable active components include, without limitation, salicylate derivatives such as acetylsalicylic acid, methyl salicylate, phenyl salicylate, methyl salicylate, acetylsalicylic acid, salicylsalicylic acid, magnesium salicylate, choline salicylate, choline magnesium salicylate, and triethanolamine salicylate. To this end, it should be understood that the topical composition can include more than one active component as desired.

The salicylate derivatives to be employed in the inventive methods are individually well recognized in the art. Moreover, they are available commercially and, thus, need not be described in detail herein.

In accordance with the invention, the active component is present within a pharmaceutically acceptable solubilizer. In this regard, the solubilizer includes any recognized component(s) that is capable of at least partially dissolving or solubilizing one or more of the active components.

By "partially dissolving or solubilizing" it is meant that at least a portion of the one or more active components exists as a molecule or ion in the solubilizer. To this end, in a preferred embodiment, the at least partially dissolved or solubilized active component(s) will provide a substantially homogenous solution. Furthermore, in accordance with another embodiment of the invention, the solution comprising at least partially dissolved or solubilized active component(s) may appear colorless, clear, translucent, transparent, opaque, or any desired color depending on the particular components, e.g., active component(s), solubilizer(s), and additives, present within the composition.

In a preferred embodiment, the solubilizer includes one or more solvents that are pharmaceutically acceptable for application to skin or exposed tissue of a non-human including, but not limited to, alcohols including denatured alcohols, such as ethanol; glycols and polyalkylene glycols, such as butylene glycol, polyethylene glycol and polypropylene glycol; polysorbates, sorbitols and water.

For examples, suitable solvents include $C_1$-$C_4$ alcohols, $C_1$-$C_4$ alkylene glycols, $C_1$-$C_4$ polyalcohols, $C_1$-$C_4$ polyalkylene glycols, sorbates, polysorbates, benzyl alcohol, triglycerides, and water.

Specific examples of suitable components for the solvent mixture include propylene glycol, glycerin, ethanol, isopropyl alcohol and the like. Specifically, propylene glycol, glycerin, and isopropyl alcohol, ethanol, and the like, which are recognized in the art as safe for topical application to non-human skin and/or exposed tissue, are discussed in more detailed below.

Propylene glycol can serve as a moisturizer and can produce a pleasant emollient feel when applied to the skin. Furthermore, propylene glycol also has the added advantage of being a mild germicide. However, in excessive concentrations the germicidal properties can potentially irritate sensitive skin.

Glycerine (glycerol; 1,2,3-propanetriol) can serves as a mild astringent that can cause increased blood flow to the skin and can allow the propylene glycol to carry the at least one salicylate derivative into the epidermis and/or hair follicles. Excessive amounts of glycerine may allow the propylene glycol to penetrate below the epidermis, which would be undesirable.

Isopropyl alcohol (isopropanol; 2-propanol) can serve as a bulk solvent for the other ingredients of the topical compositions. Isopropyl alcohol can also serve to dissolve oils and grease, thus cleaning the skin and permitting a more intimate contact of the other ingredients with the skin. Isopropyl alcohol is also less dehydrating to the skin than ethanol and, because it is less polar, it is a better solvent for use in conjunction with a salicylate derivative, e.g., acetylsalicylic acid. It is believed, however, that ethanol in the composition would not adversely effect the effectiveness of the composition.

The solvent mixture can include mixtures of the foregoing components. From a commercial standpoint, the solvent mixture preferably includes one or more of propylene glycol, glycerin, and isopropyl alcohol.

Solvent mixtures employed in the present invention will preferably have a polarity such that the active component will not readily precipitate from the solution at ordinary room temperature. More preferably, the active component, e.g., acetylsalicylic acid, should not readily precipitate from the solvent mixture at temperatures at or above approximately 50 degrees F. To this end, the solvent mixture can comprise one or more of propylene glycol, glycerin, isopropyl alcohol, ethanol, polyethylene glycol and water.

In one example of a suitable embodiment, the solvent mixture comprises propylene glycol in the range of approximately 5 to 15% by volume, glycerin in the range of approximately 1 to 10% by volume, and the remainder of the solvent mixture being comprised of one or more of isopropyl alcohol, ethanol, or water. For example, the remainder of the solvent mixture can comprise at least approximately 20, 30, 40, 50, 60, 70 or even 80% or more by volume of isopropyl alcohol.

Additional embodiments of the present invention employ a solvent mixture comprising propylene glycol in an amount of approximately 10 to 15% by volume, glycerin in an amount of approximately 2 to 4% by volume, with the remainder of said solvent mixture comprising isopropyl alcohol or, alternatively, a combination of isopropyl alcohol and ethanol and/or water. In another embodiment, said combination of isopropyl alcohol and ethanol and/or water is preferably comprised of at least approximately 7% by volume of isopropyl alcohol.

The active component(s) are present in an amount effective to prevent, treat or aid in the healing of a non-human animal skin or tissue disorder. The precise amount of active component is dependent upon both the disorder and the animal being treated and optimization would therefore involve only routine experimentation.

For example, as stated above, the active component employed in the methods of the present invention can comprise acetylsalicylic acid. While the following discussion focuses on the use of acetylsalicylic acid, the invention is not limited to this embodiment.

In this embodiment, the acetylsalicylic acid is present in an amount of at least 1%, alternatively at least 2%, or even 3% or at least 4%, with at least about 5% by weight per volume of the solvent mixture being preferred. In certain environments, the acetylsalicylic acid is present in an amount greater than about 10% by weight or even 15% by weight. Due to solubility concerns, the acetylsalicylic acid or other salicylate derivative is typically not greater than 18% by weight per unit volume of the solvent mixture In another embodiment, the topical compositions can include one or more silicone additives.

The addition of a silicone additive into the topical compositions is capable of improving, among other properties, the shelf life of the composition, the feel on the skin, and the therapeutic strength of the topical composition. In particular, the introduction of a silicone additive can reduce the amount of drying and/or peeling of the skin that may result from administering the solvent mixtures of the present invention to mammalian skin. Moreover, a silicone additive can also provide an improved "feel" upon use. For example, such an additive can reduce potential stinging and burning sensations, particularly when used in connection with hair removal procedures. With regard to enhancement of the therapeutic strength of the topical compositions of the present invention, a silicone additive is capable of facilitating the contact between the active component and the non-human animal skin surface.

Suitable silicone additives for use with the present invention include siloxanes and/or polysiloxanes. Specific examples of suitable compounds include decamethylcyclopentasiloxane, octamethylcyclotetrasiloxane, cyclomethicone, dimethicone and mixtures thereof.

The amount of the optional one or more silicone additives present in the topical composition is ultimately dependent upon the combination of desired properties for the resulting topical composition. In one embodiment, a silicone additive is preferably introduced in an amount such that the volume ratio of silicone additives to the active component/solubilizer combination is in the range of from approximately 20:1 to approximately 1:20. Specific examples of preferred volume ratios of active component/solubilizer to silicone additive will be dependent on the components and the use environment, but typically are in the range of from about 1:1 to about 10:1, preferably from about 2:1 to about 5:1 or even from about 3:1 to about 4:1.

The topical compositions according to the present invention can be in any suitable form for application to animal skin or tissue. Examples of suitable forms include, but are not limited to, a gel, lotion, ointment, oil, cream, milk, liniment, salve, paste, stick, liquid, spray, soap, shampoo, conditioner, balm, solution, suspension, dispersion, emulsion or wax.

In this regard, the compositions can include other components that are not inconsistent with the desired form and/or use of the composition. That is, additional components can be introduced to provide additional functionality to the resulting topical composition, such as components and additives directed to a particular fragrance, color, and or viscosity.

Moreover, additional components can be added depending on the particular animal which is to be treated.

The topical compositions according to the present invention can be produced by techniques recognized in the art for providing topical compositions. Since such techniques are known in the art they need not be described in detail here.

The present invention also relates to methods of using the topical composition in a variety of veterinary applications. In this regard, the topical compositions according to the present invention can be employed in a connection with non-human animals, preferably, but not limited to mammals and in particular, hair and/or fur bearing mammals such as dogs, cats, horses, and cows, among others.

Examples of suitable veterinary applications include, but are not limited to, the treatment of infections including bacterial infections, viral infections, fungal infections, parasitic infections, viruses including warts, bites including insect bites, burns including sunburns, skin conditions including acne, cuts, scratches, lacerations, abrasions, ulcerations, inflammations, rashes, cold sores, skin cancer, scar tissue, stretch marks, removal of foreign objects such as splinters, hair related disorders such as ingrown hair, razor burn, as well as itching, or any combination thereof.

In addition, the present invention relates to the use of the topical compositions for the treatment of open wounds, cuts, scratches, ulcerations or abrasions, including, but not limited to, those wounds, cuts, scratches, etc that are inhabited by insects or insect larvae.

For example, one embodiment of the invention relates to a method of treating a non-human skin irritation comprising topically administering to the skin irritation a therapeutically effective amount of a topical composition comprising: (1) an active component comprising acetylsalicylic acid; at least partially dissolved in (2) at least one pharmaceutically acceptable solubilizer.

In another embodiment, the present invention relates to a method of preventing insects from inhabiting a wound, comprising topically administering to the wound of a non-human animal, an effective amount of a topical composition comprising: (1) an active component comprising at least one salicylate derivative; at least partially dissolved in (2) at least one pharmaceutically acceptable solubilizer.

In still another embodiment, the present invention further provides a method of preventing insect bites comprising topically administering to non-human skin an effective amount of a topical composition comprising: (1) an active component comprising at least one salicylate derivative; at least partially dissolved in (2) at least one pharmaceutically acceptable solubilizer.

In yet another embodiment, the present invention provides a method of treating a softened ungulate hoof comprising topically administering to the softened hoof a therapeutically effective amount of a topical composition comprising: (1) an active component comprising at least one salicylate derivative; at least partially dissolved in (2) at least one pharmaceutically acceptable solubilizer.

Another embodiment of the present invention provides a method of reducing the flow of blood from a bleeding, non-human animal wound, comprising topically administering to the wound a therapeutically effective amount of a topical composition comprising: (1) an active component comprising at least one salicylate derivative; at least partially dissolved in (2) at least one pharmaceutically acceptable solubilizer.

In addition, the invention includes methods of treating a non-human animal, comprising contacting the skin or exposed tissue of a non-human animal with a material impregnated or at least partially saturated with a topical composition comprising: (1) an active component comprising at least one salicylate derivative; at least partially dissolved in (2) a pharmaceutically acceptable solubilizer; wherein the active component is present in a therapeutically effective amount to prevent, treat or aid in the healing of a skin or tissue disorder.

In this embodiment of the invention, the material can be any object recognized as being suitable for contacting with skin or exposed tissues. Specific examples of suitable materials include, but are not limited to, bandages, tapes, patches, strips, gauze, pads, cotton products including cotton balls, and cotton swabs, tissues, wipes, fabrics, applicators, dressing or any combination thereof.

Moreover, the amount of topical composition introduced into, onto or in connection with the material is dependent upon the ultimate end use of the material.

While this invention has been described in connection with preferred embodiments, it is not intended to limit the scope of the invention to the particular embodiments set forth, but on the contrary, it is intended to cover such alternatives, modifications, and equivalents as may be included within the spirit and scope of the invention as defined by the appended claims. For example, there are numerous variations and combinations of components and or conditions, e.g., active component, concentrations, desired solubilizers, the particular animal and/or dermatological disorder to be treat and the like that can be used to optimize the results obtained from the described methods. To this end, one skilled in the art will appreciate that in practicing the process of this invention, only reasonable and routine experimentation will be required to optimize such conditions.

EXAMPLE

One example of a suitable topical composition for use in the present invention comprises mixing together the following components:

| | |
|---|---|
| Isopropyl Alcohol | 100–500 ml, including 200-300 ml, preferably 280-290 ml; |
| Glycerin | 1-30 ml, including 5-15 ml, preferably 7-10 ml; |
| Propylene Glycol | 10-100 ml, including 30-50 ml, preferably 35-45 ml; |
| Cyclomethicone | 1-30 ml, including 5-15 ml, preferably 8-10 ml; |
| Water | 1-100 ml, including 10-90 ml, also preferably not greater than 85-90 ml; and |
| Acetylsalicylic Acid | 100-500 mg, including 200-400 mg, also preferably not greater than 350–400 mg. |

What is claimed is:

1. A method of treating a dermatological disorder of a non-human animal, the method comprising topically administering to a hair-related dermatological disorder comprising ingrown hair, razor burn or combinations thereof, of a non-human mammal chosen from dogs, horses, cows, and pigs, a therapeutically effective amount of a topical composition consisting essentially of:
    a) an active component comprising at least one salicylate derivative chosen from acetylsalicylic acid, methyl salicylate, phenyl salicylate, choline salicylate, magnesium salicylate; choline magnesium salicylate; salicylsalicylic acid; and triethanolamine salicylate where the active component is present in amount such that the active component does not readily precipitate out of the composition at a temnerature of 50° F.;
    (b) at least two pharmaceutically acceptable solvents acceptable for application to non-human skin or exposed tissue chosen from propylene glycol, glycerin, isopropyl alcohol, ethanol, polyethylene glycol, water, or any combinations thereof, wherein the at least two solvents include propylene glycol in an amount of about 5 to about 15% by vol. of the solvents (b) and glycerin in an amount of about 1 to about 10% by vol. of the solvents (b), and further wherein at least a portion of the active component of a) is at least partially dissolved in the solvents (b); and
    (c) at least one silicone additive that comprises a siloxane or a polysiloxane, wherein the volume ratio of silicone additive to solvents (b) is not greater than 1:3.

2. The method of claim 1, wherein the at least one salicylate derivative is acetylsalicylic acid.

3. The method of claim 1, wherein the at least one silicone additive comprises decamethylcyclopentasiloxane, octamethylcyclotetrasiloxane or dimethicone.

4. The method of claim 1, wherein the at least one silicone additive comprises cyclomethicone or dimethicone.

5. A method of treating a dermatological disorder of a non-human animal, the method comprising topically administering to a hair-related dermatological disorder comprising ingrown hair, razor burn or combinations thereof, of a non-human mammal chosen from dogs, horses, cows, and pigs, a therapeutically effective amount of a topical composition comprising:
    a) acetylsalicylic acid, which is present in an amount not greater than 18% by weight per unit volume of the solvent mixture;
    (b) a solvent mixture comprising at least two pharmaceutically acceptable solvents acceptable for application to non-human skin or exposed tissue, wherein the solvent mixture comprises propylene glycol and glycerin and further wherein at least a portion of the active component of a) is at least partially dissolved in the solvent mixture (b); and
    (c) at least one silicone additive, which additive comprises a siloxane or a polysiloxane, wherein the volume ratio of silicone additive: solvent mixture (b) is not greater than 1:3.

6. The method of claim 5, wherein the solvent mixture further comprises at least one solvent chosen from $C_1$-$C_4$ alcohols, $C_1$-$C_4$ alkylene glycols, $C_1$-$C_4$ polyalcohols, $C_1$-$C_4$ polyalkylene glycols, sorbates, polysorbates, benzyl alcohol, triglycerides, and water.

7. The method of claim 5, wherein the solvent mixture further comprises isopropyl alcohol, ethanol, polyethylene glycol, water, or any combinations thereof.

8. The method of claim 5 wherein the at least one silicone additive comprises decamethylcyclopentasiloxane, octamethylcyclotetrasiloxane or dimethicone.

9. The method of claim 5 wherein the at least one silicone additive comprises cyclomethicone or dimethicone.

10. The method of claim 5, wherein the solvent mixture comprises propylene glycol which is present in a range of from 5 to 15% by volume of the solvent mixture.

11. The method of claim 5, wherein the solvent mixture comprises glycerin which is present in the range of from 1 to 10% by volume of the solvent mixture.

12. A method of treating a dermatological disorder of a non-human animal, the method comprising topically administering to a hair-related dermatological disorder comprising ingrown hair; razor burn or combinations thereof, of a non-human mammal chosen from dogs, horses, cows, and pigs, a therapeutically effective amount of a topical composition comprising:
    (a) acetylsalicylic acid, which is present in an amount not greater than 18% by weight per unit volume of the solvent mixture (b);
    (b) a solvent mixture comprising
        (i) propylene glycol, which is present in an amount of in an amount of about 5 to about 15% by vol. of the solvent mixture (b),
        (ii) glycerin, which is present in an amount of in an amount of about 1 to about 10% by vol. of the solvent mixture (b). and
        (iii) isopropyl alcohol, and
    (c) a silicone additive comprises which comprises at least one of cyclomethicone or dimethicone, wherein the volume ratio of silicone additive to solvent mixture (b) is not greater than 1:3.

* * * * *